United States Patent
Paul

(10) Patent No.: US 7,727,265 B2
(45) Date of Patent: Jun. 1, 2010

(54) BONE SUPPORT PLATE ASSEMBLY

(76) Inventor: Kamaljit S. Paul, 3220 Old Orchard La., Oshkosh, WI (US) 54902-7330

( * ) Notice: Subject to any disclaimer, the term of this patent is extended or adjusted under 35 U.S.C. 154(b) by 756 days.

(21) Appl. No.: 11/136,179

(22) Filed: May 23, 2005

(65) Prior Publication Data

US 2005/0216011 A1   Sep. 29, 2005

Related U.S. Application Data

(60) Division of application No. 10/662,194, filed on Sep. 12, 2003, now abandoned, and a continuation-in-part of application No. 10/337,001, filed on Jan. 6, 2003, now abandoned, which is a continuation of application No. 09/838,646, filed on Apr. 19, 2001, now Pat. No. 6,503,250.

(60) Provisional application No. 60/491,642, filed on Jul. 30, 2003, provisional application No. 60/486,539, filed on Jul. 10, 2003, provisional application No. 60/253,437, filed on Nov. 28, 2000.

(51) Int. Cl.
*A61B 17/88* (2006.01)
*A61B 17/80* (2006.01)
(52) U.S. Cl. .......................... 606/281; 606/70; 606/71; 606/286; 606/289; 606/295; 606/296
(58) Field of Classification Search ................. 606/61, 606/69–71, 279, 281
See application file for complete search history.

(56) References Cited

U.S. PATENT DOCUMENTS 2,406,832 A   9/1946   Hardinge 2,440,123 A   4/1948   Smith (Continued)

FOREIGN PATENT DOCUMENTS

DE   2808971   9/1979

(Continued)

OTHER PUBLICATIONS

Premier Anterior Cervical Plate System, Slides series from presentation led by T.A. Zdeblick, MD & H.N. Herkowitz MD, Nov. 2000, pp. 1-5 and 7-8, Kohler, WI.

*Primary Examiner*—Eduardo C Robert
*Assistant Examiner*—Julianna N Harvey
(74) *Attorney, Agent, or Firm*—Thomas D. Wilhelm; Wilhelm Law, S.C.

(57) ABSTRACT

A sliding bone support plate assembly comprises at least first and second plates which slide with respect to each other, varying the length of the plate assembly by plate-on-plate sliding after bone screws mount the plate assembly to vertebrae in a recipient. The plates comprise cooperating sliding structures which cooperate with each other to interconnect the plates to each other and to facilitate sliding movement of the plates with respect to each other. Such sliding accommodates varying the length of the plate assembly, and relieving stress which would otherwise be imposed on the plate assembly by post-procedural settling of respective vertebrae to which the plates are mounted without requiring any movement of a plate with respect to a bone to which that plate is mounted. The plate assembly is fabricated using bio-compatible, bio-stable materials which are safe for extended use in a living human, and which are not generally assimilated.

33 Claims, 5 Drawing Sheets

U.S. PATENT DOCUMENTS

| | | | |
|---|---|---|---|
| 2,443,363 A | 6/1948 | Townsend et al. | |
| 2,486,303 A | 10/1949 | Longfellow | |
| 4,246,660 A | 1/1981 | Wevers | |
| 4,503,848 A | 3/1985 | Caspar et al. | |
| 4,513,744 A | 4/1985 | Klaue | |
| 4,887,595 A | 12/1989 | Heinig et al. | |
| 5,084,049 A | 1/1992 | Asher et al. | |
| 5,324,290 A | 6/1994 | Zdeblick et al. | |
| 5,344,421 A | 9/1994 | Crook | |
| 5,352,224 A | 10/1994 | Westermann | |
| 5,405,391 A | 4/1995 | Hednerson et al. | |
| 5,423,816 A | 6/1995 | Lin et al. | |
| 5,470,333 A * | 11/1995 | Ray | 606/61 |
| 5,549,612 A | 8/1996 | Yapp et al. | |
| 5,569,251 A | 10/1996 | Baker et al. | |
| 5,578,034 A | 11/1996 | Estes | |
| 5,616,142 A * | 4/1997 | Yuan et al. | 606/61 |
| 5,616,144 A | 4/1997 | Yapp et al. | |
| 5,676,666 A | 10/1997 | Oxland et al. | |
| 5,681,311 A | 10/1997 | Foley et al. | |
| 5,728,127 A | 3/1998 | Asher et al. | |
| 5,827,286 A | 10/1998 | Incavo et al. | |
| 5,876,402 A | 3/1999 | Errico et al. | |
| 5,904,683 A | 5/1999 | Pohndorf et al. | |
| 5,951,558 A | 9/1999 | Fiz | |
| 5,954,722 A | 9/1999 | Bono | |
| 6,017,345 A | 1/2000 | Richelsoph | |
| 6,030,389 A | 2/2000 | Wagner et al. | |
| 6,106,557 A | 8/2000 | Robioneck et al. | |
| 6,129,730 A | 10/2000 | Bono et al. | |
| 6,139,550 A | 10/2000 | Michelson | |
| 6,152,927 A | 11/2000 | Farris et al. | |
| 6,159,213 A | 12/2000 | Rogozinski | |
| 6,193,721 B1 | 2/2001 | Michelson | |
| 6,206,882 B1 | 3/2001 | Cohen | |
| 6,224,602 B1 | 5/2001 | Hayes | |
| 6,235,034 B1 | 5/2001 | Bray | |
| 6,238,396 B1 | 5/2001 | Lombardo | |
| 6,241,731 B1 | 6/2001 | Fiz | |
| 6,258,089 B1 | 7/2001 | Campbell et al. | |
| 6,287,309 B1 | 9/2001 | Baccelli et al. | |
| 6,293,949 B1 | 9/2001 | Justis et al. | |
| 6,306,136 B1 * | 10/2001 | Baccelli | 606/61 |
| 6,306,139 B1 | 10/2001 | Fuentes | |
| 6,340,362 B1 | 1/2002 | Pierer et al. | |
| 6,364,881 B1 | 4/2002 | Apgar et al. | |
| 6,383,186 B1 | 5/2002 | Michelson | |
| 6,398,783 B1 | 6/2002 | Michelson | |
| 6,402,756 B1 | 6/2002 | Ralph et al. | |
| 6,428,542 B1 | 8/2002 | Michelson | |
| 6,454,771 B1 | 9/2002 | Michelson | |
| 6,458,133 B1 | 10/2002 | Lin | |
| 6,471,706 B1 | 10/2002 | Schumacher et al. | |
| 6,503,250 B2 * | 1/2003 | Paul | 606/69 |
| 6,533,786 B1 | 3/2003 | Needham et al. | |
| 6,602,255 B1 | 8/2003 | Campbell et al. | |
| 6,602,256 B1 | 8/2003 | Hayes | |
| 6,626,907 B2 | 9/2003 | Campbell et al. | |
| 6,755,833 B1 | 6/2004 | Paul et al. | |
| 6,761,719 B2 | 7/2004 | Justis et al. | |
| 7,097,645 B2 | 8/2006 | Michelson | |
| 2002/0151899 A1 | 10/2002 | Bailey et al. | |
| 2003/0018335 A1 | 1/2003 | Michelson | |
| 2003/0045880 A1 | 3/2003 | Michelson | |
| 2003/0074001 A1 | 4/2003 | Apfelbaum et al. | |
| 2003/0083658 A1 | 5/2003 | Hawkes et al. | |
| 2003/0212399 A1 * | 11/2003 | Dinh et al. | 606/61 |
| 2004/0006343 A1 | 1/2004 | Sevrain | |
| 2004/0019353 A1 | 1/2004 | Freid et al. | |
| 2004/0092939 A1 | 5/2004 | Freid et al. | |
| 2004/0127903 A1 | 7/2004 | Schlapfer et al. | |
| 2004/0158251 A1 | 8/2004 | Morrison et al. | |

FOREIGN PATENT DOCUMENTS

| | | |
|---|---|---|
| DE | 4409833 | 10/1995 |
| EP | 1169971 | 1/2002 |
| FR | 1505513 | 12/1967 |
| FR | 2778088 | 11/1999 |
| WO | WO 99/04718 | 2/1999 |
| WO | WO 9904718 A1 * | 2/1999 |
| WO | WO 00/24325 | 5/2000 |
| WO | WO 00/64359 | 11/2000 |
| WO | WO 01/26566 | 4/2001 |
| WO | WO 01/26567 | 4/2001 |
| WO | WO 02/085226 | 10/2002 |
| WO | WO 03/000148 | 1/2003 |
| WO | WO 03/063714 | 8/2003 |

* cited by examiner

BONE SUPPORT PLATE ASSEMBLY

CROSS-REFERENCE TO RELATED APPLICATIONS

This application claims priority under 35 U.S.C. §120 to application Ser. No. 10/662,194 filed Sep. 12, 2003, to application Ser. No. 10/337,001 filed Jan. 6, 2003, and to its parent application Ser. No. 09/838,646 filed Apr. 19, 2001, now U.S. Pat. No. 6,503,250 issued Jan. 7, 2003, and claims priority, under 35 U.S.C. §119, to its parent Provisional application Ser. No. 60/253,437 filed Nov. 28, 2000, as well as under 35 U.S.C. §119 to Provisional Applications 60/486,539 filed Jul. 10, 2003 and 60/491,642 filed Jul. 30, 2003, all the above of which are herein incorporated by reference in their entireties.

BACKGROUND

The present invention relates to devices for the fixation and/or support of bones. In particular, the present invention relates to bone support plate assemblies for the fixation and/or support of bones of the spinal column, thus spinal plate assemblies. The plate assemblies of the present invention have particular application in situations where compressional or "settling" forces, as well as torsional and flexing forces on a spinal plate, which supports "fixed" vertebrae, cause significant stressing, and potential failure of the spinal plate and/or plate components.

Vertebral fixation has become a common approach to treating spinal disorders, fractures, and the like, and for fusion of vertebrae at the time such fixation is instituted. Namely, one or more vertebrae are fixed in position relative to one or more other vertebrae above, e.g. toward the head from, and/or below, e.g. toward the coccyx from, the vertebrae being fixed. Generally, a spinal plate is the device of choice used for mechanically supporting such vertebral fixation. A typical spinal plate includes a plate having a plurality of bone support apertures therethrough. A plurality of fasteners, i.e., bone screws, are generally positioned into and through respective bone support apertures of the plate to secure the spinal plate to bone, such as to respective upper and lower supporting adjacent spinal vertebrae. The screws are fastened to the respective support vertebrae to secure the spinal plate to the respective vertebrae. In general, such plate and screw assemblies can be utilized for e.g. anterior fixation of the e.g. cervical, lumbar, and/or thoracic portions of the spine.

The basis of anterior fixation or plating is to approach the spine from an anterior or anterio-lateral direction, and to use the screws to solidly mount the spinal plate to the affected vertebrae. In some instances, in addition to the application of a spinal plate, graft material may be incorporated into the procedure in an attempt to permanently fuse together adjacent vertebrae. The graft material can be e.g. of bone grafts obtained from bones of the recipient or from another individual.

A first common and undesirable result associated with use of conventional such spinal plates is the tendency of the bone screws to "back out," or pull away from the bone into which they are fixed. This problem occurs primarily as a result of the normal torsional and bending motions of the human body and spine as the recipient/patient goes about routine daily activities. This is a particularly important problem because, as the screws become loose and pull away from the bone, the heads of the screws can rise above the surface of the spinal plate and can even work their way completely out of the bone. While this condition can cause extreme discomfort for the recipient, this condition can also create a number of potentially serious physiological problems given the significant amount of nervous and vascular structures located at or near the potential locations of anterior spinal plate fixations.

A number of designs have been proposed in attempts to prevent screws from pulling away from the bone and/or to prevent the screws from backing out or pulling away from the surface of the spinal plate. Such mechanisms used to prevent bone screws from pulling out of bones include cams which engage and lock the screws, and the use of expanding head screws which expand outwardly when adequate force is applied thereto to engage the holes in the spinal plate. All of these designs have detriments including potential for breakage or requiring particular precision and alignment in their application in order to work correctly. Additionally, loose components and accessories of spinal plates which address the "backing-out" problem can get dropped and/or misplaced while the vertebral fixation surgical procedure is taking place, prolonging and complicating the procedure as well as creating substantial risk of harm to the recipient.

A second common result associated with use of such spinal plates is the tendency of the vertebrae being "fixed" to settle after the spinal plate affixation procedure. Such settling of the "fixed" vertebrae relative to each other is a response to the normal loading of the spine as the recipient/patient carries on routine daily activities. Such settling of the "fixed" vertebrae adds compression forces to the above-listed forces which cause the bone screws to "back out" or pull away from the bone into which they were fixed. Zdeblick et al (U.S. Pat. No. 5,324,290) attempted to address the problem of compression forces in the context of treating vertebral burst fractures, but fails to provide any functional means to prevent the screws pulling away as a result of torsional and flexing forces. Zdeblick et al also fails to provide any structure in the plate assembly which relieves the stress imposed on the plate by the vertebral settling.

My U.S. Pat. No. 6,503,250 teaches use of slot-shaped apertures which enables longitudinal translation of the bone screws in the slot-shaped apertures with respect to the plate in cooperation with post-procedural settling of the vertebrae. Such translation of the bone screws requires that the bone screws not be locked to the plate, and is accompanied by movement of the bone screws with respect to the plate, along the longitudinal axes of the slots, typically along the longitudinal axis of the plate. Such settling of the bones, such movement of the bone screws with respect to the plate, is also accompanied by movement of the plate with respect to one or more of the vertebrae to which the plate is mounted. Such movement of the plate with respect to the bone can, in some instances, have undesirable consequences.

Therefore, it is an object of the invention to provide spinal plate assemblies which accommodate rigid bone-to-bone fixation and provide bone support for such fixation, such as e.g. adjacent or second adjacent vertebrae, while allowing post-procedural compression between the respective bones, e.g. post procedural bone-to-bone movement, without requiring any movement of any bone screw in a slot-shaped aperture with respect to the respective plate.

It is a further object of the invention to provide spinal plate assemblies wherein the bone screws do not need to move with respect to the plate assembly in order for stress, potentially imposed on the plate assembly by post-procedural settling of the vertebrae, to be relieved or avoided.

Yet a further object of the invention is to provide spinal plate assemblies having first and second sliding plates which are adapted and configured to provide plate-on-plate sliding of the first and second plates, with respect to each other, in order to relieve a substantial portion of the stress which would otherwise be imposed on the respective plate assembly by post-procedural vertebral settling.

Still a further object of the invention is to provide spinal plate assemblies which accommodate bone-to-bone settling while providing bone support for such fixation, while accommodating post procedural compression between the respective bones, and while maintaining rigid, unmoving fixation between the plate and the respective bones/vertebrae.

It is a further object of the invention to provide bone support plate assemblies, e.g. spinal plate assemblies, which accommodate bone-to-bone settling while providing bone support for such fixation, while accommodating post procedural compression between the respective bones, without requiring, or enabling, any movement of any plate with respect to a bone to which such plate is mounted.

SUMMARY

A sliding bone support plate assembly comprises at least first and second plates which slide with respect to each other, thus to vary the overall length of the bone support plate assembly by plate-on-plate sliding. The first and second plates comprise cooperating first and second sliding structures which cooperate with each other both to interconnect the plates to each other and to facilitate sliding movement of the first and second plates with respect to each other. Such sliding movement accommodates varying the first overall length of the bone support plate assembly, in order to relieve a substantial portion of the stress which would otherwise be imposed on the bone support plate assembly by post-procedural settling of respective vertebral structure to which the plates are mounted. The bone support plate assembly is fabricated using bio-compatible and bio-stable materials which are safe for use in a living human body for an extended period of time, and which materials are not generally assimilated into the living human body.

Preferably, the plate-on-plate sliding is accomplished by one or more insert-accepting tracks on the first plate, and one or more sliding inserts on the second plate, and wherein at least one of the sliding inserts extends continuously between opposing sides of the respective sliding insert.

In a first family of embodiments, a sliding bone support plate assembly has a first overall length, and comprises first and second plates which slide with respect to each other thus to vary the overall length of the bone support plate assembly. The first plate has at least a first bone fastener aperture for receiving therethrough at least a first bone fastener adapted to fasten the first plate to a first vertebra. The second plate has at least a second bone fastener aperture for receiving therethrough at least a second bone fastener adapted to fasten the second plate to a second vertebra. The first and second plates comprise cooperating first and second sliding structures which cooperate with each other and thereby enable interconnecting the first and second plates with corresponding longitudinal sliding movement of the first and second plates with respect to each other, thus to accommodate varying the first overall length of the bone support plate assembly. The plate assembly is fabricated using bio-compatible and bio-stable materials which are safe for use in a living human body for an extended period of time, and which are not assimilated into such living human body. The sliding of the first and second plates with respect to each other facilitates post-procedural settling of the first and second vertebrae with respect to each other, preferably post-procedural compression of the respective vertebrae, and relieving, from the plate assembly, of a substantial amount, typically all, of the stress potentially imposed on the plate by post-procedural vertebral settling.

The recited post-procedural settling typically, and desirably, results in maintaining the respective e.g. first and second vertebrae under post-procedural axial loading.

In some embodiments, the sliding bone support plate assembly further comprises cover apparatus associated with at least one of the bone fastener apertures, the cover apparatus automatically extending over a bone fastener which is driven in a respective one of the bone fastening apertures, when a cover land associated with the respective bone fastener moves past the cover apparatus.

In some embodiments, the sliding bone support plate assembly further comprises temporary length retention structure, effective to temporarily fix the first overall length of the sliding bone support plate assembly at a temporary overall length prior to and/or during installation of the sliding bone support plate assembly in a recipient user.

In some embodiments, the temporary length retention structure comprises at least one set screw.

In some embodiments, the first plate comprises a first coupling screw aperture, and the second plate comprises a second coupling screw aperture adapted to be aligned with the first coupling screw aperture at the temporary overall length, and the temporary length retention structure comprises a coupling screw adapted to connect the first and second coupling screw apertures to each other, thereby to fix the overall length of the sliding bone support plate assembly at the temporary overall length.

In some embodiments, the sliding structure on the first plate comprises a channel, and the sliding structure on the second plate comprises a rail sliding in the channel.

In some embodiments, the sliding structure on the first plate comprises first and second channels, and the sliding structure on the second plate comprises first and second rails sliding in the first and second channels.

In some embodiments, the sliding structure on the first plate comprises first and second channels, and the sliding structure on the second plate comprises first and second opposing lateral sides, the first and second channels on the first plate receiving the opposing lateral sides of the second plate, the opposing lateral sides of the second plate sliding with respect to the channels of the first plate.

In some embodiments, the sliding structures of the first and second plates comprise cooperating tongue and groove structures.

In some embodiments, the first plate comprises a first major surface, the second plate comprises a second major surface, a first portion of the first major surface of the first plate facing a second portion of the second major surface of the second plate, at least substantial portions of the cooperating sliding structures on the first and second plates being embodied in the facing major surfaces of the first and second plates.

In some embodiments, the cooperating sliding structures comprise dovetail structures as parts of the facing portions of the facing major surfaces. Preferably, the cooperating sliding structures comprise at least two female dovetail sliding elements, and at least two male dovetail sliding elements cooperating with the at least two female dovetail sliding elements, on the facing portions of the facing major surfaces.

In preferred embodiments, each of the at least first and second plates comprises at least first and second bone fastener apertures adapted to receive bone fasteners therethrough, each of the first and second plates further comprising a retainer which extends between the respective first and second bone fastener apertures, and which automatically extends over a land associated with a compatible bone fastener which is driven through one of the first and second bone fastener apertures, when the land associated with the respective bone fastener moves past the retainer.

In preferred embodiments, the first and second plates are adapted to slide with respect to each other during post-procedural settling of the first and second vertebrae with respect to each other, without corresponding movement of the first and second plates with respect to underlying ones of the first and second vertebrae to which the first and second plates are mounted.

In a second family of embodiments, the invention comprehends a sliding bone support plate assembly having a first overall length, and comprising first and second plates which slide with respect to each other thus to vary the first overall length of the bone support plate assembly. The first plate has at least a first insert accepting track, each insert accepting track having a first interior side X and a second interior side Y. The second plate has at least a first insert structure. Each insert structure has a first lateral side X' and a second lateral side Y'. Side X' of the first insert structure is in sliding communication with side X of the first insert accepting track. Side Y' of the first insert structure is in sliding communication with side Y of the first insert accepting track. At least one insert structure extends continuously between side X' and side Y', and each of the first and second plates further comprises at least one bone fastener aperture adapted to receive a bone fastener therethrough thus to facilitate mounting the respective plate to at least first and second vertebrae. The plate assembly is structured from bio-compatible and bio-stable materials which are safe for use in a living human body for an extended period of time, and which are not assimilated into the living human body.

In some embodiments, the sliding plate assembly includes temporary length retention structure, which optionally comprises at least one coupling screw, optionally a set screw.

In some embodiments, the first plate comprises a first coupling screw aperture, and the second plate comprises a second coupling screw aperture adapted to be aligned with the first coupling screw aperture at a temporary overall length, and wherein the temporary length retention structure comprises a coupling screw adapted to connect the first and second coupling screw apertures to each other, thereby to fix the overall length of the sliding bone support plate assembly at the temporary overall length.

In some embodiments, the insert-accepting track on the first plate comprises first and second channels, and the insert structure on the second plate comprises first and second rails sliding in the first and second channels.

In some embodiments, the insert-accepting track on the first plate comprises first and second channels, and the insert structure on the second plate comprises first and second opposing lateral sides, the first and second channels on the first plate receiving the opposing lateral sides of the second plate, and the opposing lateral sides of the second plate sliding with respect to the channels of the first plate.

In some embodiments, the sliding insert-accepting track of the first plate and the insert structure of the second plate comprise cooperating tongue and groove structures.

In some embodiments, at least substantial portions of the insert-accepting track and the insert structure are embodied in facing major surfaces of the first and second plates.

In preferred embodiments, the insert-accepting track and the insert structure comprise dovetail structures on facing portions of major surfaces of the first and second plates. Preferably, the insert-accepting track and the insert structure comprise at least two female dovetail sliding elements, and at least two male dovetail sliding elements cooperating with the at least two female dovetail sliding elements, on the facing portions of the facing major surfaces.

In a third family of embodiments, the invention comprehends a sliding bone support plate assembly having a first overall length, and comprising first and second plates which slide with respect to each other thus to vary the first overall length of the bone support plate assembly. The first plate has one or more longitudinally extending sliding apertures. The second plate has one or more longitudinally extending sliding inserts, each having a width extending between opposing outer sides thereof. Each combination of one of the one or more sliding apertures and one of the one or more sliding inserts is adapted and configured with one or more insert-accepting tracks which facilitate sliding engagement of the respective sliding insert and sliding aperture, at least one of the one or more sliding inserts, in the sliding apertures, extending continuously between the opposing sides of the respective sliding insert; the plate assembly being structured from bio-compatible and bio-stable materials which are safe for use in a living human body for an extended period of time, and which are not assimilated into the living human body.

In some embodiments, the first plate comprises a first coupling screw aperture, and the second plate comprises a second coupling screw aperture adapted to be aligned with the first coupling screw aperture at the temporary overall length, and wherein the temporary length retention structure comprises a coupling screw adapted to connect the first and second coupling screw apertures to each other, thereby to fix the overall length of the sliding bone support plate assembly at the temporary overall length.

In a fourth family of embodiments, the invention comprehends a sliding bone support plate assembly having a first overall length, and comprising first and second plates which slide with respect to each other thus to vary the first overall length of the bone support plate assembly. The first plate has a first length, first opposing side edges, and at least a first bone fastener aperture adapted to receive a first bone fastener therethrough thus to facilitate mounting the first plate to a first vertebra of a recipient user. The first plate comprises a first major surface, and a male dovetail structure extending outwardly from the first major surface and along the first length of the first plate. The first major surface comprises a wing element thereof between the male dovetail structure and a respective one of the first side edges. The second plate has a second length, second opposing side edges, and at least a second bone fastener aperture adapted to receive a second bone fastener therethrough thus to facilitate mounting the second plate to a second vertebra of the recipient user. The second plate comprises a second major surface facing the first major surface of the first plate, and a female dovetail structure extending inwardly from the second major surface and along the second length of the second plate. The second major surface comprises a plate land element thereof between the female dovetail structure and a respective one of the second side edges adjacent the wing element of the first major surface. The male and female dovetail structures cooperate with each other and thereby enable interconnecting and engagement of the first and second plates to each other along the male and female dovetail structures, as well as along the first and second major surfaces, including engagement of the wing element and the plate land element with each other, such that longitudinal sliding movement of the first and second plates with respect to each other is facilitated, thus to accommodate varying the first overall length of the bone support plate assembly. As with other embodiments, the plate assembly can be fabricated using bio-compatible and bio-stable materials which are safe for use in a living human body for an extended period of time, and which are not assimilated into such living human body. Sliding of the first and second plates with respect to each other facilitates post-procedural settling of the first and second vertebrae with respect to each other, and corresponding post-procedural compression of the respective vertebrae, and relieving, from the plate assembly, of stress imposed by such post-procedural vertebral settling.

In preferred embodiments, when the first and second plates are mounted to underlying first and second bones, magnitude of movement of the first and second plates with respect to each other corresponds generally with magnitude of movement of the underlying first and second bones with respect to each other.

In a fifth family of embodiments, the invention comprehends sliding bone support plate assembly having a first overall length, and comprising first and second plates which slide with respect to each other thus to vary the first overall length of the bone support plate assembly. The first plate has at least a first bone fastener aperture for receiving therethrough at least a first bone fastener adapted to fasten the first plate to a first vertebra, and the second plate has at least a second bone fastener aperture for receiving therethrough at least a second bone fastener adapted to fasten the second plate to a second vertebra, the first and second plates comprising cooperating first and second sliding structures which enable interconnecting the first and second plates with corresponding longitudinal sliding movement of the first and second plates with respect to each other, thus to accommodate varying the first overall length of the bone support plate assembly, the plate assembly being structured from bio-compatible and bio-stable materials which are safe for use in a living human body for an extended period of time, and which are not assimilated into such living human body, sliding of the first and second plates with respect to each other facilitating post-procedural settling of such first and second vertebrae with respect to each other, the first and second plates being adapted to slide with respect to each other during post-procedural settling of the first and second vertebrae, without corresponding movement of the first and second plates with respect to underlying ones of the first and second vertebrae to which the first and second plates are mounted.

In a sixth family of embodiments, the invention comprehends a method of installing a bone support plate assembly in a recipient thereof, the bone support plate assembly having a first overall length, and comprising first and second plates which are slidingly engaged with each other, so as to slide with respect to each other thus to vary the first overall length of the bone support plate assembly. The method comprises placing the bone support plate assembly at a mounting location in a recipient user of the bone support plate assembly; fastening the first and second plates to first and second bones of the recipient user of the bone support plate assembly; and releasing, as necessary, any fixation structure or device which temporarily fixes the overall length of the bone support plate assembly, so as to accommodate sliding of the first and second plates with respect to each other, and correspondingly accommodating post-procedural settling of such first and second bones with respect to each other.

In a seventh family of embodiments, the invention comprehends a method of installing a bone support plate assembly in a recipient thereof, the bone support plate assembly having a first overall length, and comprising first and second plates which are slidingly engaged with each other, so as to slide with respect to each other thus to vary the first overall length of the bone support plate assembly. The method comprises temporarily fixing the overall length of the bone support plate assembly; placing the bone support plate assembly at a mounting location in a recipient user of the bone support plate assembly; fastening the first and second plates to first and second bones of the recipient user of the bone support plate assembly; and releasing the length fixation so as to accommodate sliding of the first and second plates with respect to each other, and correspondingly accommodating post-procedural settling of such first and second bones with respect to each other.

In preferred embodiments, the method comprises providing, as the bone support plate assembly, a bone support plate assembly wherein the first and second plates are adapted to slide with respect to each other during post-procedural settling of the first and second vertebrae with respect to each other, without corresponding movement of the first and second plates with respect to underlying ones of the first and second vertebrae to which the first and second plates are mounted.

Figure 1:
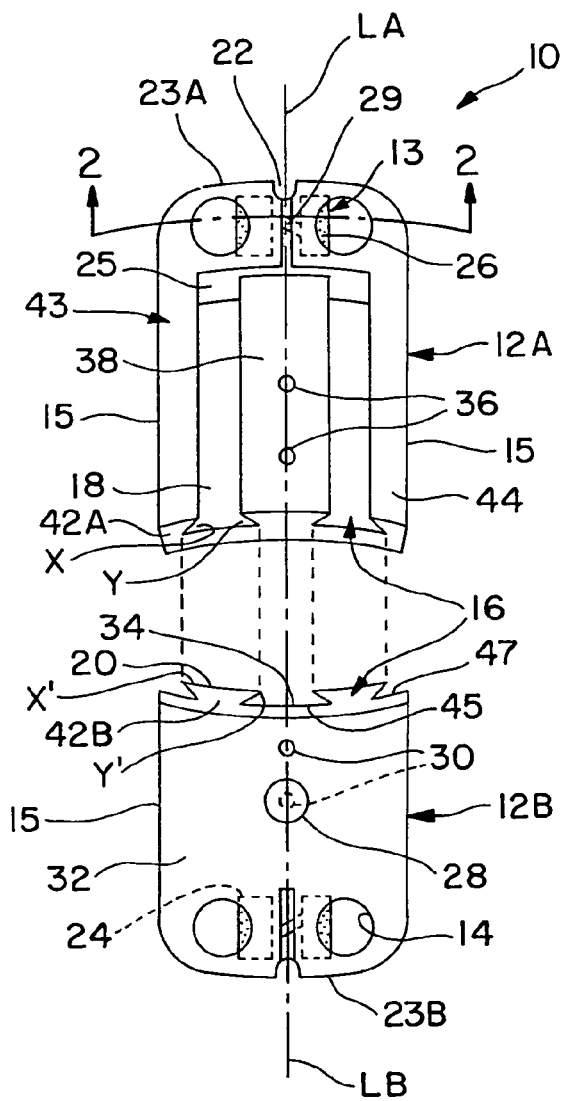
FIG. 1 shows a pictorial exploded view of a first embodiment of spinal plate assemblies of the invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 2:
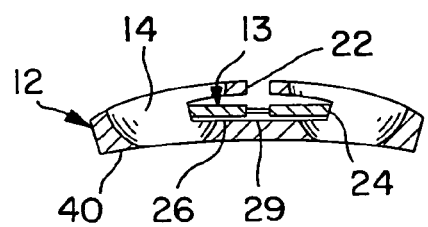
FIG. 2 shows a cross-section of the first plate of the bone support plate assembly of FIG. 1, taken at 2-2 of FIG. 1.
Figure 3:
FIG. 3 shows a pictorial view of a coupling assembly screw useful in the bone support plate assembly of FIGS. 1 and 2.

FIGS. 1-3 illustrate a first embodiment of spinal plate assemblies of the invention which are used for long-term support of bone structures, especially bone structures of the spine. As with all embodiments of the invention, the components of the bone support plate assembly of FIGS. 1-3 are fabricated of, structured from, materials which are bio-compatible and bio-stable with respect to the human body, e.g. which are safe for use in a living human body for extended periods of time, and which are not routinely assimilated by the living human body.

In general, in the embodiment of FIGS. 1-3, male dovetail structure extends as ridges from a first major surface of a first plate and slides with respect to female dovetail structure which extends as channels from a second major surface of a second plate, thus to facilitate longitudinal plate-to-plate sliding of the plates with respect to each other while coupling the plates together, and to accommodate extensions and retractions of the overall length of the plate assembly.

A coupling screw cooperates with aligned apertures in the first and second plates to set a temporary overall length of the plate assembly.

Figure 4:
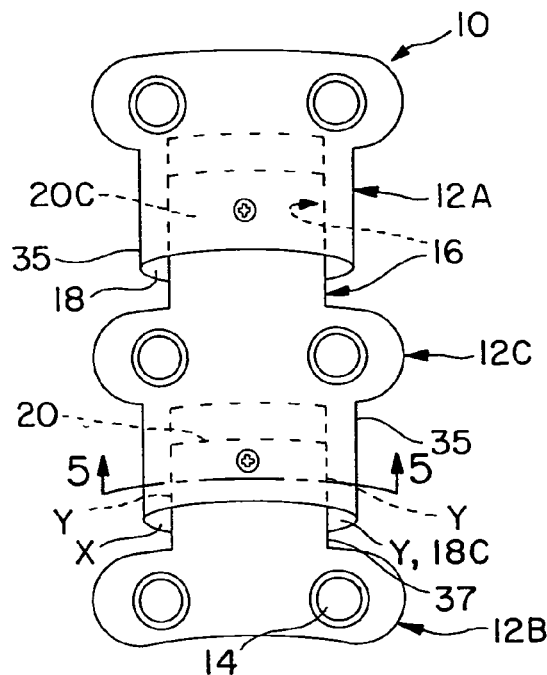
FIG. 4 shows a top view of a second bone support plate assembly of the invention.
Figure 6:
FIG. 6 shows a pictorial view of a set screw useful in the bone support plate assembly of FIGS. 4 and 5.
Figure 5:
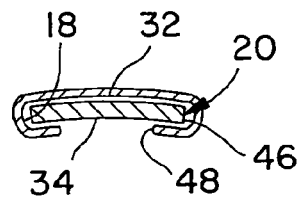
FIG. 5 shows a cross-section of the bone support plate assembly of FIG. 4 and is taken at 5-5 of FIG. 4.

FIGS. 4-6 illustrate a second embodiment of spinal plate assemblies of the invention. In general, in the embodiment of FIGS. 4-6, outer edges of sliding inserts on the first plate are received in, and slide with respect to, insert accepting tracks at a sliding aperture on the second plate, thus to facilitate longitudinal plate-to-plate sliding of the plates with respect to each other while the plates are engaged with each other, and to accommodate extensions and retractions of the overall length of the plate assembly.

A coupling set screw in the second plate can be tightened to bear against a major surface of the first plate, thus to set a temporary overall length of the plate assembly.

Figure 7:
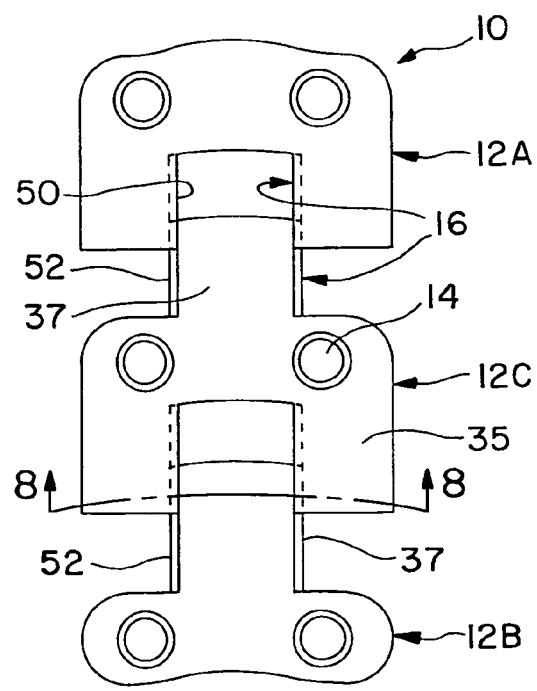
FIG. 7 shows a top view of a third bone support plate assembly of the invention.
Figure 8:
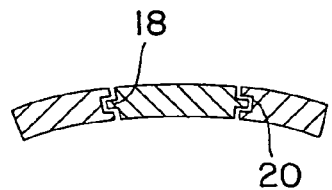
FIG. 8 shows a cross-section of the bone support plate assembly of FIG. 7 and is taken at 8-8 of FIG. 7.

FIGS. 7-8 illustrate a third embodiment of spinal plate assemblies of the invention. In general, in the embodiment of FIGS. 7-8, rails on the outer edges of sliding inserts on the first plate are received in, and slide with respect to, channels which act as insert accepting tracks at a sliding aperture on the second plate, thus to facilitate longitudinal plate-to-plate sliding of the plates with respect to each other while the plates are engaged with each other, and to accommodate extensions and retractions of the overall length of the plate assembly.

Figure 9:
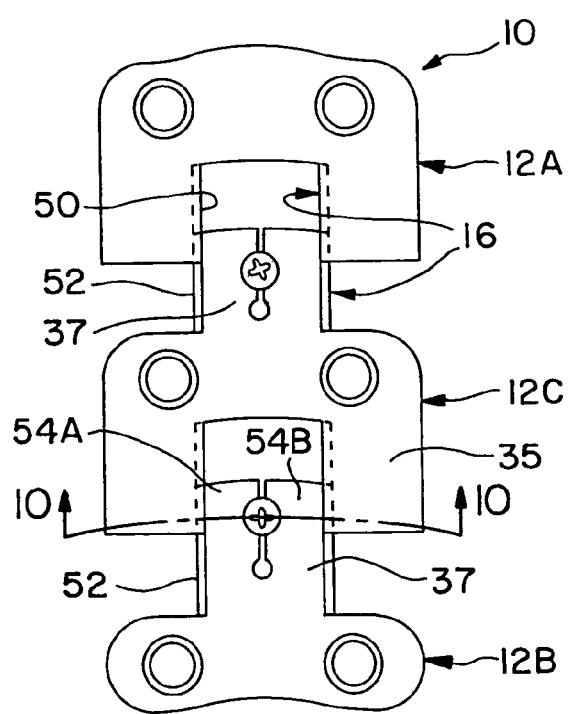
FIG. 9 shows a top view of a fourth bone support plate assembly of the invention.
Figure 10:
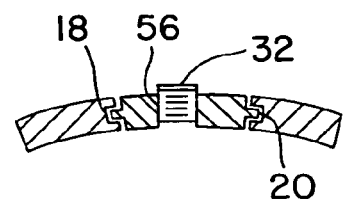
FIG. 10 shows a cross-section of the bone support plate assembly of FIG. 9 and is taken at 10-10 of FIG. 9.

FIGS. 9-10 illustrate a fourth embodiment of spinal plate assemblies of the invention. In general, in the embodiment of FIGS. 9-10, rails on the outer edges of sliding inserts on the first plate are received in, and slide with respect to, channels which act as insert accepting tracks at a sliding aperture on the second plate, thus to facilitate longitudinal plate-to-plate sliding of the plates with respect to each other while the plates are engaged with each other, and to accommodate extensions and retractions of the overall length of the plate assembly.

An expansion coupling screw in the first plate can be tightened to urge the sliding inserts against the channels, thus to bring the inserts into frictional engagement with the channels, and to enable the using surgeon to temporarily fix the overall length of the plate assembly.

When the expansion coupling screw is advanced, the screw urges the left and right elements/rails of the sliding insert on the second plate laterally against the left and right channels in the receiving aperture on the first plate, whereby the sliding inserts on the second plate are temporarily held against sliding movement with respect to the channels of the receiving aperture on the first plate. The first and second plates are thus coupled, by frictional engagement, and prevented from sliding movement with respect to each other while the expansion coupling screw is in an advanced location.

This frictional coupling engagement, and corresponding temporary fixation of length of the plate assembly, is released, and ongoing sliding of the first and second plates with respect to each other is enabled, by retracting and/or removing the expansion coupling screw, which enables the inherent resilience of the rails of the second plate to withdraw the rails from their frictional, coupling engagement with the channels on the first plate, whereby the rails freely slide with respect to the channels.

Any of the embodiments can be modified, as necessary, to provide or accommodate temporarily fixing the overall length of the plate assembly. Such temporary length fixation can be achieved, on the one hand, by internal plate assembly structure such as by cooperation of the combined features of coupling screw 28 and coupling apertures 30, 36.

On the other hand, such temporary length fixation can be achieved externally e.g. by engaging one or more plate installation tools, not shown, with the plate assembly and employing one or more features of such tool or tools to temporarily fix the length of the plate assembly while the plate assembly is in the process of being installed in the recipient user. In either case, the temporary length can be adjusted from time to time, as desired, by the surgeon during the installation procedure.

While the length of the plate assembly is temporarily fixed, in any of the embodiments, and whether by using internal or external temporary length fixation, or no length fixation, the plates can be mounted, as desired, to the vertebrae of a recipient/patient of the bone support plate assembly. Prior to completion of the surgical procedure, the surgeon releases such temporary length fixation, and can optionally remove the coupling screw or other length fixing structure from the assembly, such that the plates can slide with respect to each other after completion of the surgical procedure, whereby the plates can thereby accommodate post-procedural settling of the so-treated bones with respect to each other.

The above described plate-to-plate sliding feature, of extension and retraction in plate assemblies of the invention, accommodates post-procedure settling of the vertebrae which are being supported by the plate assembly, without putting undue stress on the plate assembly, or on the bone screws which mount the plate assembly to the bone structure of the recipient user of the plate assembly and without requiring, typically without allowing, any movement of a plate with respect to any bone/vertebra to which that particular plate is mounted e.g. by a bone screw.

Typically, the bone screw apertures are circular, and are not elongated. While some aperture elongation can be employed, while slotted apertures are within the scope of the invention, in preferred embodiments, the bone screws do not, in general, move with respect to a plate, and the plates do not move with respect to the bones/vertebrae to which they are mounted, after the plate is attached to a vertebra of a recipient/patient. Namely, the bone screws and bone screw apertures are preferably cooperatively adapted to retain the bone screws in fixed location with respect to the plate, the plate in fixed location with respect to the bone to which the plate is mounted, once the bone screws are screwed into bone structure of the recipient user/patient.

The above described capacity for the first and second plates to slide with respect to each other in the plate assemblies of the invention enables the individual plates, which are mounted to respective individual vertebrae, to move, concurrently with movement of the respective vertebrae, with concurrent plate-to-plate sliding of the plates with respect to each other, without plate-to-bone sliding with respect to each other.

The concurrent plate-to-plate sliding of the plates results in the overall length of the plate assembly automatically adjusting to the movement of the respective vertebrae without any movement between vertebrae and the respective plates. Namely, as the distance between the vertebrae changes, the overall length of the plate changes by about a corresponding amount. This adjustment of the overall length of the plate to vertebral distance changes avoids substantial build-up of stress in the connection between plate assembly and vertebrae, namely in the bone screws, as well as avoiding the corresponding plate-to-bone movement where a plate is affixed to the respective underlying bone, as the distance between vertebrae changes. While some nominal amount of residual stress may be present in the plate or bone screws, the majority of the potential stress is dissipated by the sliding of the plates with respect to each other.

Referring specifically, now, to the drawings, FIGS. 1-3 illustrate a first embodiment of 2-plate spinal plate assemblies 10 of the invention. Assembly 10 includes a first plate 12A, a second plate 12B, first and second retainers 13, and coupling screw 28. Each plate 12A, 12B includes first and second bone screw apertures 14 and opposing side edges 15. Each plate includes sliding structure 16 which facilitates sliding of the plates with respect to each other when the plates are assembled to each other to form the assembly 10. Plate 12A has a distal end 23A and a proximal end 42A. Plate 12B has a distal end 23B and a proximal end 42B.

Sliding structure 16 on the first plate 12A is illustrated in FIG. 1 as first and second female dovetail channels 18 which extend from a first major surface 43 along the length of plate 12A. Sliding plate lands 44 extend, as part of the first major surface 43 of plate 12A, between each of channels 18 and the adjacent side edges 15 of the first plate.

Sliding structure 16 on the second plate 12B is illustrated in FIG. 1 as first and second male dovetail ridges 20 which extend from second major surface 45 along the length of plate 12B. A sliding wing 47 extends, as part of the second major surface 45 of plate 12B, between each of ridges 20 and the adjacent side edge 15 of the second plate.

Retainer 13 resides in a retainer slot 22 associated with each plate 12A or 12B. Referring to FIGS. 1 and 2, slot 22 extends downwardly from the top surface of the plate, and thence left and right toward bone screw apertures 14 a distance sufficient to extend into the respective apertures 14, while providing an outer wall 24 against which retainer 13 is biased. Slot 22 extends to distal end 23A of plate 12A, whereby retainer 13 can be inserted into slot 22 from end 23. Slot 22 terminates in a dead end, short of proximal end 25 of sliding structure 16. The proximal end of slot 22 includes a relatively constricted neck portion.

Retainer 13 includes left and right retainer bands 26, and a spring 29, integral with and connected to each of bands 26. Spring 29 biases the bands 26 against the outer walls 24 of slot 22, thus bringing the bands into blocking positions extending across portions of apertures 14, as shown. Retainer 13 is thus held longitudinally in slot 22 by the resilient expansive force of spring 29 in combination with the blocking surfaces of slot 22 presented at the neck, and the dead end of the slot.

Overlying coupling apertures 30 extend along a corresponding longitudinal axis "LB" of plate 12B, at the top major surface 32 of plate 12B, through the thickness of the plate and to the bottom major surface 34.

Underlying coupling apertures 36 are spaced along a corresponding longitudinal axis "LA" of plate 12A, at the top major surface 38 of plate 12A, and extend to the bottom surface of the plate. While apertures 36 preferably extend entirely through the thickness of plate 12A to bottom major surface 40, the invention comprehends embodiments wherein apertures 36 in plate 12A are dead-end apertures; namely apertures 36 which extend into, but not through, underlying plate 12A.

FIG. 1 shows the head of coupling screw 28 overlying one of the coupling apertures 30 in plate 12B.

Plate assembly 10 is assembled and used as follows. Plates 12A and 12B are brought together with the facing proximal ends 42A and 42B of the respective plates 12A and 12B generally facing each other, and with the male and female dovetails aligned for cooperative sliding with respect to each other. The end portions of the male and female dovetail elements are then engaged, whereupon the male and female dovetail elements facilitate plate-to-plate sliding of the plates with respect to each other, while the dovetail structures slidingly couple the plates to each other. In the resulting plate assembly, the dovetail structures provide primary prevention of the plates becoming separated from each other along directions transverse to longitudinal axes "LA" and "LB". Sliding wings 47 and sliding plate lands 44 on the first and second major surfaces are engaged with each other, outwardly of the dovetail structure, to provide substantial engagement to assist in resisting of twisting movement of plates 12A and 12B with respect to each other e.g. about longitudinal axes "LA" and "LB". Placement of twisting resistance outwardly of the dovetail structure, namely toward side edges 15 from the dovetail structure, enhances the sensitivity of the plate assembly to twisting, and enables the plate to more effectively resist twisting, for a given clearance between the plates at the sliding interface. Further, employment of wings 47 and plate lands 44 can take advantage of the entire widths of plates 12A, 12B with respect to twisting resistance.

Returning specifically to the process of assembling plate assembly 10, once engaging of the dovetail structures is initiated, sliding of the plates with respect to each other is continued along the interconnected dovetail structures until a selected one of overlying coupling apertures 30 comes into overlying alignment with a selected one of underlying apertures 36, thus to define a temporary overall length of the bone support plate assembly. With the temporary length thus defined, and with overlying and underlying coupling apertures thus aligned on plates 12A and 12B, coupling screw 28 is advanced through the respective overlying coupling aperture 30 and into the respective underlying coupling aperture 36, thus temporarily fixing the length of the bone support plate assembly.

With two coupling apertures as shown in each of plates 12A and 12B, and wherein the two pairs of apertures are not simultaneously aligned, the surgeon who is installing the bone support plate assembly has 4 temporary plate assembly overall lengths from which to select before advancing the screw through one of apertures 30 and into one of apertures 36. The number of aperture-to-aperture optional temporary lengths from which the surgeon can select can be increased by increasing the number of coupling apertures in either or both of the plates. Such increased number of coupling apertures are preferably arrayed in alignment with the apertures shown, e.g. along the respective longitudinal axis.

Once the particular vertebral arrangement in the recipient user is determined during surgery, the surgeon sets an initial temporarily fixed length for the plate assembly by aligning an aperture 30 in plate 12B with an aperture 36 in plate 12A, then inserting screw 28 into the selected aperture 30. Screw 28 is then advanced through the respective overlying coupling aperture 30 and into the respective underlying aperture 36, thus to fix the temporary length of the assembly for purposes of initial installation, namely mounting the plate assembly to vertebrae of the recipient user.

Referring to the respective vertebrae being treated, as designated with respect to each other, the vertebra relatively closer to the skull is called the overlying vertebra and the vertebra relatively closer to the coccyx is referred to as the underlying vertebra.

With the temporary length set, whether an initial length or a revised length, the surgeon places the bone support plate assembly 10 on location in the recipient user, and checks that the plate assembly, at the temporarily fixed length enables advancing bone screws through apertures 14 and into bone structure of the underlying vertebra of the recipient user at optimal locations, thus to mount at least one of plate 12A or 12B, and correspondingly the assembly, to the recipient user.

If, after bone screws are advanced through plate 12A into bone of the recipient user, remaining ones of the apertures 14 are not suitably aligned with structure of the vertebrae, coupling screw 28 is loosened enough to enable sliding of plate 12B with respect to plate 12A, and the overall length of the plate assembly is thus adjusted as necessary so as to establish a suitable revised overall temporarily fixed length which accommodates securing bone screws to the vertebrae at desirable locations through plate 12B.

When a suitable revised overall temporarily fixed length has been achieved, which provides the desired alignment between the vertebrae and apertures 14 which are yet to receive bone screws, coupling screw 28 is advanced until the end of the coupling screw enters an aperture 36, or impacts upper major surface 38 of plate 12B. Where screw 28 impacts surface 38, screw 28 acts as a set screw, fixing a revised temporary overall length of the plate assembly. While the coupling screw 28 holds the revised overall length, screw holes are drilled through respective ones of apertures 14 and into the bone structure of the recipient user, and bone screws are advanced through the respective apertures 14 and into the bone structure, thus mounting plate 12B to the vertebra.

As an alternative procedure, the surgeon can set a temporary overall length of the plate assembly, suitable for installing bone screws in all of the apertures, prior to installing any of the bone screws. Thus, the adjustment of plate length, referred to above as occurring after installation of bone screws in plate 12A, can be effected prior to any of the bone screws being installed in bone structure of the recipient user.

As a bone screw is advanced past a respective band 26, spring 29 flexes resiliently, enabling the respective band 26 to move out of the way of the advancing head, or other land, of the screw. Once the head or other land passes the band, spring 29 pushes the respective band back over the head or other land and blocks reverse-direction movement of the head or other land which would tend to release the screw from the bone. Retainer 13, through bands 26, thus prevents the screws from backing out of apertures 14.

In a typical surgical procedure, and with plates 12A and 12B slidingly coupled to each other, e.g. plate 12A is first mounted to the vertebra of the recipient user which underlies the plate, whereby the vertebra of the recipient user is correspondingly temporarily mounted to the respective plate 12A or 12B.

Subsequently, bone screws are advanced through apertures 14 in the remaining plate, e.g. plate 12B, to mount the remaining plate to a second vertebra which underlies the remaining plate.

With both of plates 12A and 12B mounted to vertebrae which underlie the respective plates, coupling screw 28 is withdrawn from its fixation of the overall length of the plate assembly, and is preferably removed from the plate assembly, whereupon plates 12A and 12B are free to slide with respect to each other along the respective sliding structures as the respective vertebrae, to which they are mounted, move with respect to each other after completion of the surgical procedure, the plates being coupled, and held, to each other by the dovetail design of sliding structures 16.

Post procedure, and now referring to the spinal column as a whole, and the vertebrae directly affected by the bone support plate assembly, it is desirable to enable the overlying vertebra, which is disposed relatively toward the skull to settle with respect to the underlying vertebra, which is disposed relatively toward the coccyx, whereby the overlying vertebra exerts compression loading on the underlying vertebra, namely axial loading on the underlying vertebra.

Such compression loading is accompanied by a tendency, while the recipient user is in an upright orientation, for the overlying vertebra to move downwardly under the force of gravity toward the underlying vertebra, thus to reduce the distance between the overlying and underlying vertebrae. However, as the overlying vertebra tends to settle, the overlying vertebra urges downwardly the bone screws in the overlying vertebra. This downward force causes the respective overlying plate, e.g. plate 12A, toward the skull, to slide downwardly with respect to the underlying plate, e.g. plate 12B, toward the coccyx, namely along the length of the plate assembly toward apertures 14 in plate 12B.

Accordingly, such capacity for sliding movement of plate 12A toward plate 12B accommodates post-procedural compression of the respective underlying and overlying vertebrae, which is considered to be a desirable response of the vertebrae being so treated.

While the above description has related to the embodiments of FIGS. 1-3, a wide variety of sliding structures, and locations of sliding structures are contemplated as being within the scope of the invention. Referring to dovetail structures 18, 20, the structures of the dovetails, themselves, can be modified in any way desired so long as the dovetail structures cooperate to retain the plates together, and accommodate longitudinal sliding movement of the plates with respect to each other.

Further, the locations of the sliding structures can be moved away from the major faces of the plates, and onto edges of the plates. Indeed, the embodiments of FIGS. 4-10 disclose various other sliding structures, generally located at the outer edges of plate 12B.

Finally, the location, and especially the structure, of coupling screw 28, if any, can take on a variety of embodiments, also as illustrated in the embodiments of FIGS. 4-10.

Turning now to the embodiments of FIGS. 4-6, a 3-plate assembly 10 is illustrated. The plate assembly of FIGS. 4-6 includes a first end plate 12A, a second end plate 12B, and an intermediate plate 12C. Plate 12A has female sliding apertures 18 proximate the outer edges of the plate. Plate 12B has a male sliding insert 20. Plate 12C has a second male sliding insert 20C at outer edges of the plate end which is received in, engages with, and cooperates with, aperture 18 of plate 12A. Plate 12C further has a second female sliding aperture 18C at the end of plate 12C which cooperates with insert 20C on plate 12C.

As illustrated in FIG. 5, outer edges 46 of the male sliding inserts function as the male sliding structure 20 which interfaces with, and slides with respect to, the female apertures 18. The embodiments of male sliding structures 20 in e.g. FIG. 5 extend generally at right angles to the major surfaces 32 and 34 of e.g. plate 12B, between surfaces 32 and 34.

Referring to FIGS. 4 and 5, female aperture 18, e.g. aperture 18C of plate 12C, is defined in general as an opening on the end of plate 12C which faces plate 12B. Aperture 18, as illustrated, also includes a second portion of the opening at the bottom of plate 12C adjacent surface 34 of plate 12B, the second portion of the opening extending along the underside of plate 12C and being defined at edges 48.

Plates 12A and 12C can be thought of as each having a receiving end 35 associated with the respective apertures 18; and plates 12B and 12C can be thought of as each having an insert end 37 associated with the respective male inserts 20. Each such aperture end has an overlying coupling aperture 30 extending therethrough. Coupling set screws 28 are positioned in the coupling apertures. With the insert ends of plates 12B and 12C in the respective apertures, and extending to at least beyond apertures 30 on plates 12A and 12C, such that insert ends of plates 12B, 12C underlie the respective apertures 30, coupling set screws 28 can be advanced into frictional engagement with the underlying inserts at the insert ends of plates 12B and 12C, thus to set a temporarily fixed overall length of the plate assembly.

As with the embodiment of FIGS. 1-3, with the temporarily fixed length preferably set, the surgeon places the bone support plate assembly 10 on location in the recipient user. The surgeon then checks that the plate assembly, at the temporarily fixed length, enables advancing bone screws through apertures 14 of plates 12A, 12B, and 12C as desired, and into bone structure of the underlying vertebra of the recipient user at optimal locations, thus to suitably mount plates 12A, 12B, and optionally 12C, and correspondingly the assembly, to the recipient user.

If the apertures are suitably aligned, the surgeon proceeds with installation. If some, but not all, of the apertures are suitably aligned with bone structure, one or both of coupling screws 28 are loosened enough to enable sliding of plates 12A, 12B, and/or 12C with respect to each other in order to bring apertures 14 in each of plates 12A, 12B, and 12C, as desired, into alignment with suitable vertebrae to facilitate mounting the plate assembly to respective ones of the vertebrae in the recipient user. The plates are then slid to desired locations to bring apertures 14 into alignment with desired vertebral structure for inserting bone screws into the vertebrae.

Once the surgeon is satisfied with the alignment of apertures 14, the coupling screws are again advanced to fix the length of the overall plate structure, and the surgeon proceeds with installing the plate assembly in the recipient user as described with respect to FIGS. 1-3.

In the 3-plate assembly, each of the top and bottom plates, namely plates 12A and 12B are necessarily mounted to vertebrae; while mounting plate 12C to a vertebra is optional. Plate 12C may or may not be mounted directly to a vertebra through apertures 14, depending on the needs of the surgical procedure, and the judgement of the surgeon.

As an alternative, the surgeon can mount any one of plates 12A, 12B, 12C to an underlying vertebra, and then adjust the length of the plate assembly to bring the bone screw apertures 14 into alignment with vertebrae as desired, and subsequently mount bone screws through such apertures 14. After such adjustment of length, the length can again be temporarily fixed if desired, or not if the surgeon prefers to be able to make length adjustments in real time during the installation procedure.

With plates 12A and 12B, and optionally 12C mounted to vertebrae in the recipient user, such coupling screws 28 as are still tight to control length of the plate assembly, whether in whole or in part, are loosened, and are preferably removed from the plate assembly, whereupon plates 12A, 12B, and 12C are free to slide/move with respect to each other as the respective vertebrae, to which the plates are mounted, move with respect to each other, after completion of the surgical procedure.

The sliding and compression loading with the embodiments of FIGS. 4-6 work the same in the embodiments of FIGS. 4-6 as in the embodiments of FIGS. 1-3.

Turning now to the embodiments of FIGS. 7-8, another 3-plate assembly 10 is illustrated. The plate assembly of FIGS. 7-8 includes a first end plate 12A, a second end plate 12B, and an intermediate plate 12C. Plate 12A has inwardly-disposed sliding channels 50 which extend along the length of the aperture end of the plate and which operate as female sliding structure. Plate 12B has outwardly-disposed rails 52 which extend along the length of the insert end of the plate and which operate as male sliding structure. Plate 12C has a second set of rails 52 at outer edges of the plate end which are received in, and which cooperate with, channels 50 of plate 12A. Plate 12C further has a second set of channels 50 at the end of plate 12C, which cooperate with rails 52 of plate 12B.

FIG. 8 illustrates the cooperation of the channels and rails in cooperating sliding engagement with each other. Rails 52 function as the male sliding structure. Channels 50 interface with, and slide with respect to, rails 52. Channels 50 and rails 52 extend generally along the lengths of the respective plates. In the embodiments of FIGS. 7-8, the female end of a respective plate 12A or 12C extends generally alongside and outwardly of the male insert of corresponding plate 12B or 12C; whereas in the embodiments of FIGS. 4-6 the female end of a respective plate generally extends over the top, as viewed in FIG. 5, of the male insert.

Plates 12A and 12C can be thought of as each having a receiving end 35 associated with the respective channels 50. Plates 12B and 12C can be thought of as each having an insert end 37 associated with the respective rails 52.

As with the embodiments of FIGS. 1-6, the surgeon places the bone support plate assembly 10 on location in the recipient user. The surgeon adjusts the length of the plate assembly so as to enable advancing bone screws through apertures 14 of plates 12A, 12B, and 12C as desired, and into bone structure of the underlying vertebra of the recipient user at optimal locations, thus to suitably mount plates 12A, 12B, and optionally 12C, and correspondingly the assembly, to the recipient user.

In the 3-plate assembly, each of the top and bottom plates, namely plates 12A and 12B are necessarily mounted to vertebrae; while mounting of plate 12C to a vertebra is optional. Plate 12C may or may not be mounted directly to a vertebra through apertures 14, depending on the needs of the surgical procedure, and the judgement of the surgeon.

With plates 12A and 12B, and optionally 12C mounted to vertebrae in the recipient user, plates 12A, 12B, and 12C are free to slide/move with respect to each other as the respective vertebrae, to which the plates are mounted, move with respect to each other, after completion of the surgical procedure.

The sliding and compression loading with the embodiments of FIGS. 7-8 work the same in the embodiments of FIGS. 7-8 as in the embodiments of FIGS. 1-6.

Turning now to the embodiments of FIGS. 9-10, a 3-plate assembly 10 is illustrated. The plate assembly of FIGS. 9-10 includes a first end plate 12A, a second end plate 12B, and an intermediate plate 12C. Plate 12A has inwardly-disposed sliding channels 50 which extend along the length of the aperture end of the plate and which operate as female sliding structure. Plate 12B has outwardly-disposed rails 52 which extend along the length of the insert end of the plate and which operate as male sliding structure. Plate 12C has a second set of rails 52 at outer edges of the plate end which are received in, and which cooperate with, channels 50 of plate 12A. Plate 12C further has a second set of channels 50 at the end of plate 12C which cooperate with, and receive, rails 52 of plate 12B.

FIG. 10 illustrates in cross-section the cooperation of the channels and rails in cooperating sliding engagement with each other. Rails 52 function as the male sliding structure. Channels 50 interface with, and slide with respect to, rails 52. Channels 50 and rails 52 extend generally along the lengths of the respective plates. In the embodiments of FIGS. 9-10, the female end of a respective plate 12A or 12C extends generally alongside and outwardly of the corresponding male insert in plate 12B or 12C.

Plates 12A and 12C can be thought of as each having a receiving end 35 associated with the respective channels 50. Plates 12B and 12C can be thought of as having an insert end 37 associated with the respective rails 52.

The insert ends are each divided into first and second prongs 54A and 54B. Each insert end includes a coupling aperture 56 between the respective prongs. A coupling set screw 28 in aperture 56 can be advanced to spread prongs 54A and 54B away from each other, and can be retracted to release prongs 54A and 54B from such spread. As prongs 54A and 54B are spread, the rails 52 on the outer edges of the prongs frictionally engage, and thereby become coupled to, plates 12A or 12B as indicated at respective channels 50 of the receiving ends of the corresponding plates 12A, 12B. With rails 52 in channels 50, the coupling set screw is advanced sufficiently to frictionally engage and couple the rails in the channels thereby to temporarily fix the overall length of the plate assembly at an initial setting.

The embodiment of FIGS. 9-10 differs from the previous embodiments in that the insert structure at insert ends 37 in FIGS. 9-10 is discontinuous from side to side, e.g. rail to rail. By contrast, the insert structure of the embodiments of FIGS. 1-8 is continuous between opposing sides of the insert structure. For example, referring to FIG. 1, each of the male dovetails 20, acting as an insert, is continuous between a first side "X'" and a second side "Y'". Each of the female dovetails 18, acting as an insert accepting track, has a first interior side "X" and a second interior side "Y" which engagingly mate with the male sides "X'" and "Y'" of dovetail 18, for sliding communication therewith.

Similarly, the inserts of the embodiments of FIGS. 4-8 are continuous between left and right opposing edges of the inserts. While discontinuous inserts are thus contemplated as included within the scope of the invention, continuous inserts are preferred as having superior strength where material selection and dimensions are otherwise equal.

As with the embodiments of FIGS. 1-8, with the temporarily fixed length set, the surgeon places the bone support plate assembly 10 on location in the recipient user. The surgeon then checks that the plate assembly, at the temporarily fixed length, is compatible with advancing bone screws through apertures 14 of at least one of plates 12A and 12B, and 12C as desired, and into bone structure of the underlying vertebrae of the recipient user at optimal locations, thus to suitably mount plates 12A and 12B, and optionally 12C, and correspondingly the assembly, to the recipient user.

If the apertures are suitably aligned, the surgeon proceeds with installation. If one or more of the apertures are not suitably aligned with bone structure, one or both of the coupling screws 28 in plates 12B and 12C are loosened enough to enable sliding of at least one of plates 12A, 12B, and/or 12C with respect to at least one other of the plates in order to bring apertures 14 in each of plates 12A, 12B, and 12C, as desired, into alignment with suitable vertebrae to facilitate mounting the plate assembly to respective ones of the vertebrae in the recipient user. The plates are then slid to desired locations to bring apertures 14 into alignment with desired vertebral structure for inserting bone screws into the vertebrae.

Once the surgeon is satisfied with the alignment of the apertures 14 of interest, the coupling screws are again advanced to fix the length of the overall plate structure, and the surgeon proceeds with installing the plate assembly, or completion of installing of the plate assembly, in the recipient user.

With plates 12A and 12B, and optionally 12C mounted to vertebrae in the recipient user, coupling screws 28 are loosened, and are preferably removed from the plate assembly, whereupon plates 12A, 12B, and 12C are free to slide/move with respect to each other as the respective vertebrae, to which the plates are mounted, move with respect to each other, after completion of the surgical procedure.

The sliding and compression loading with the embodiments of FIGS. 9-10 work the same in the embodiments of FIGS. 9-10 as in the embodiments of FIGS. 1-8.

Figure 11:
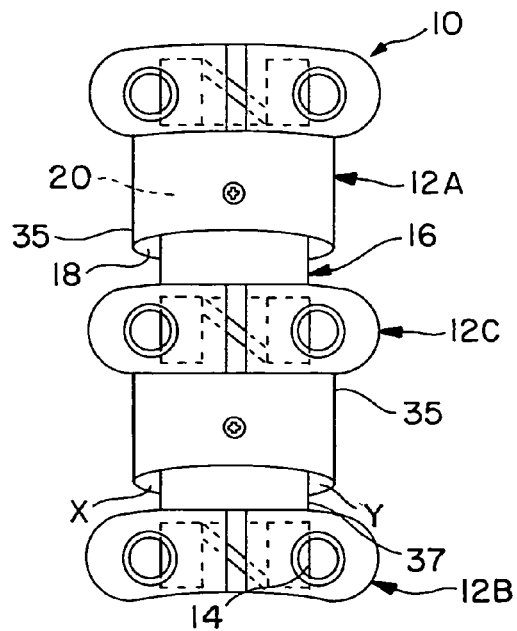
FIGS. 11 and 12 show top and side views of a plate assembly as in FIGS. 4-6, and including retainer slots and retainers as in FIGS. 1-3.
Figure 12:
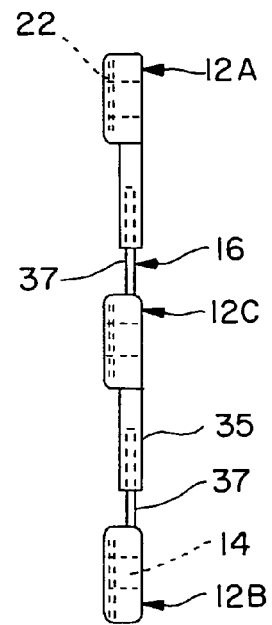

FIGS. 11 and 12 show top and side views of a 3-plate assembly as in FIGS. 4-6, and include retainer slots 22 and retainers 26 as in FIGS. 1-3.

Figure 13:
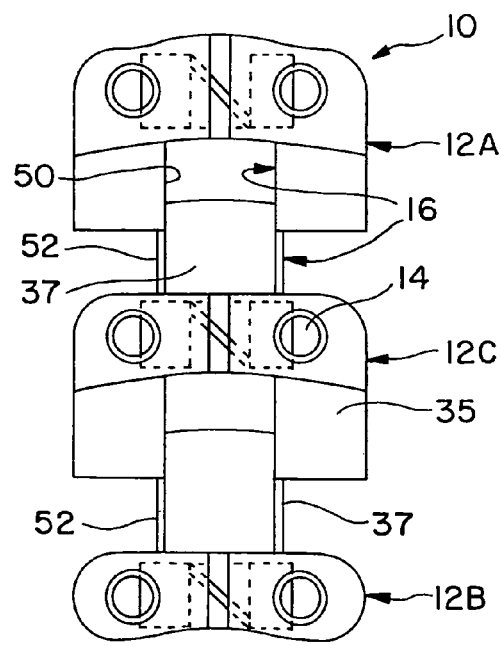
FIGS. 13 and 14 show top and side views of a plate assembly as in FIGS. 7 and 8, and including retainer slots and retainers as in FIGS. 1-3.
Figure 14:
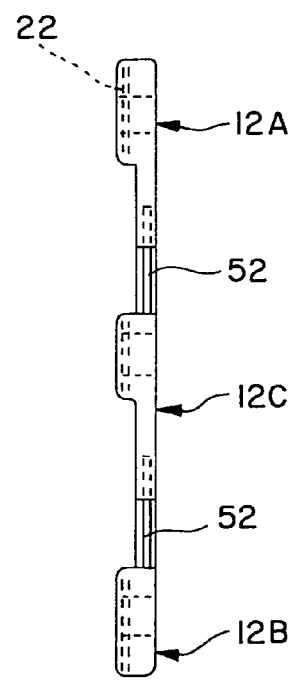

FIGS. 13 and 14 show top and side views of a 3-plate assembly as in FIGS. 7 and 8, and including retainer slots 22 and retainers 26 as in FIGS. 1-3.

Figure 15:
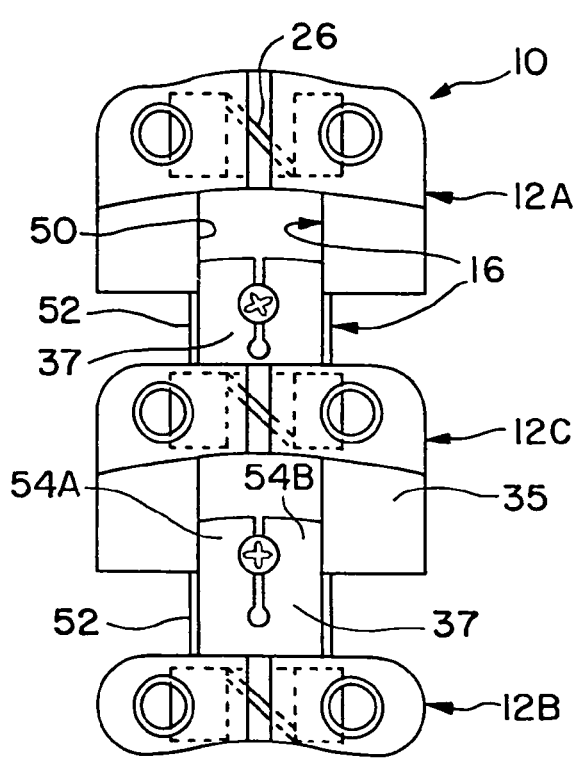
FIGS. 15 and 16 show top and side views of a plate assembly as in FIGS. 9 and 10, and including retainer slots and retainers as in FIGS. 1-3.
Figure 16:
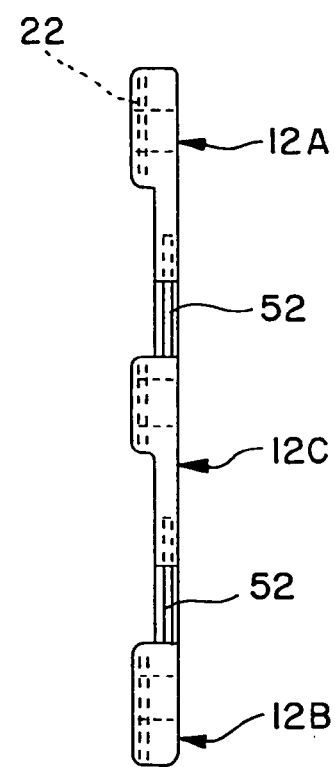

FIGS. 15 and 16 show top and side views of a 3-plate assembly as in FIGS. 9 and 10, and including retainer slots 22 and retainers 26 as in FIGS. 1-3.

While a single embodiment of retainer structure 13 is illustrated in FIGS. 1-2, a wide variety of retainer structures are known, and all conventional retainer structures and cover structures are contemplated to be compatible with respective embodiments of the plate-to-plate sliding assemblies disclosed herein. In addition to the illustrated embodiment, there can be mentioned, for example and without limitation, cover plates, locking heads, locking inserts including snap locks, covering screws, covering cams, and the like. Preferred retainer structures automatically cover the screw head or other screw land when the respective screw land is driven past the retaining structure, thereby ensuring accomplishment of an additional step in the surgical procedure.

While channels 50 have been shown at the receiving end of the plate and rails 52 have been illustrated at the insert end of the plate, such channels and rails can well be reversed. Indeed, mating structure other than channels and rails can be used, so long as the respective structure assists in mounting the plates to each other, and accommodates the recited sliding movement of the plates with respect to each other.

The plates of the plate assemblies of the invention are so joined to each other, e.g. by such cooperating lengths of channels 50 and rails 52, that the plates can slide with respect to each other while the axes of the respective plates remain in relatively fixed relation with respect to each other. Thus, plate assemblies of the invention resist bending and/or twisting loads while providing sufficient clearance between the sliding elements thereof to accommodate the recited sliding movement without binding of the sliding elements with respect to each other.

A salient feature of all embodiments of the invention is that the distance of post-procedural movement of any of e.g. plates 12A, 12B, 12C with respect to any underlying bone to which the respective plate is mounted, is limited to less, preferably substantially less, than the most extreme normal distance, of contemplated post-procedural bone settling.

While post-procedural bond-to-bone settling is highly desirable, post-procedural movement of a bone, with respect to a plate to which the bone is mounted, is generally undesirable. Accordingly, in the most highly preferred embodiments of this invention, such bone-to-plate movement is nil, or substantially nil.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method of installing a bone support plate assembly in a patient, the method comprising:
   (a) placing the bone support plate assembly at a mounting location in the patient, the bone support plate assembly having a length and comprising a plurality of plate members, including a first plate member adapted to be mounted to a first bone and a second plate member adapted to be mounted to a second bone, the first plate member having a first distal end which defines a first end of the bone support plate assembly and a first proximal plate member end, the second plate member having a second distal end which defines a second end of the bone support plate assembly and a second proximal plate member end, the plurality of plate members being slidingly engaged with each other such that respective adjacent ones of the plate members can slide with respect to each other;
   (b) attaching the so-assembled bone support plate assembly to such first and second bones by attaching the first plate member to such first bone and attaching the second plate member to such second different bone; and
   (c) during the surgical procedure, releasing any fixation internal to the bone support plate assembly between the first and second ends of the bone support plate assembly, which plate assembly fixation impedes, by such frictional engagement, or threaded coupling engagement, respective ones of the plate members from sliding with respect to each other such that the respective plate members can slide freely with respect to each other, in extension and retraction, after completion of the surgical procedure.

2. A method as in claim 1, comprising releasing any length fixation effected by threaded coupling structure from coupling engagement which impedes sliding of respective ones of the first and second plate members with respect to each other.

3. A method as in claim 1 further comprising bone-fastener-receiving apertures in the bone support plate assembly, the attaching of the so-assembled bone support plate assembly to such underlying first and second bones further comprising driving bone fasteners through ones of the bone-fastener-receiving apertures and into such underlying first and second bones, and wherein such first and second underlying bones, to which the bone support plate assembly is attached, are first and second vertebrae.

4. A method as in claim 1, comprising releasing any length fixation effected by frictional engagement structure, from frictional, engagement which impedes sliding of respective ones of the plate members with respect to each other.

5. A method as in claim 1 wherein the method provides the long-term support of the bones and wherein each of the first and second plate members is made from material selected from the group consisting of titanium and stainless steel.

6. A method as in claim 1 wherein the bone support plate assembly is a spinal plate assembly and wherein the bone support plate assembly is attached to first and second vertebrae.

7. A method as in claim 1, further comprising bone-fastener-receiving apertures in the bone support plate assembly, the attaching of the so-assembled bone support plate assembly to such bone structure further comprising driving bone fasteners through ones of the bone-fastener-receiving apertures and into such first and second bone structures, the bone support plate assembly further comprising cover apparatus spanning two such bone-fastener-receiving apertures, the cover apparatus automatically extending over a bone fastener which is driven, in a respective one of the bone-fastener-receiving apertures, and past retainer structure on the cover apparatus.

8. A method of providing long-term support of bone structure in a patient, by a surgical procedure, the method comprising:
   (a) placing, at a mounting location in the patient, a bone support plate assembly which is not routinely assimilated by the patient's body, the bone support plate assembly comprising a plurality of plate members, including
      (i) a first plate member adapted to be mounted to first bone structure, and
      (ii) a second plate member adapted to be mounted to second different bone structure,
      the first plate member having a first distal end which defines a first end of the bone support plate assembly and a first proximal plate member end, the second plate member having a second distal end which defines a second end of the bone support plate assembly and a second proximal plate member end, respective ones of the plate members being slidingly engaged with each other such that respective adjacent ones of the plurality of plate members can slide with respect to each other;
   (b) attaching the bone support plate assembly to such to such first and second bone structures by attaching the first plate member to such first bone structure and attaching the second plate member to such second different bone structure;
   (c) during the surgical procedure, releasing from fixation any internal plate assembly structure which is fixing the length of the bone support plate assembly by frictional engagement or threaded coupling, and which plate assembly structure is, by such frictional engagement or threaded coupling engagement, impeding sliding of respective ones of the plurality of plate members with respect to each other such that the respective plate members can slide freely with respect to each other in extension and retraction, after completion of the surgical procedure; and
   (d) accommodating post-procedural settling of such first and second bone structures with respect to each other without movement of either of the first and second plate members with respect to such bone structure to which the respective plate member is attached.

9. A method as in claim 8 comprising releasing threaded coupling structure from coupling engagement with at least one of the first and second plate members.

10. A method as in claim 8 further comprising bone-fastener-receiving apertures in the bone support plate assembly, the attaching of the so-assembled bone support plate assembly to such bone structure further comprising driving bone fasteners through ones of the bone-fastener-receiving apertures and into such first and second bone structures, and wherein such first and second bone structures to which the attachment is made are first and second vertebrae.

11. A method as in claim 8 comprising releasing frictional engagement structure from any frictional engagement which impedes sliding of respective ones of the plate members with respect to each other.

12. A method as in claim 8, further comprising bone-fastener-receiving apertures in the bone support plate assembly, the attaching of the so-assembled bone support plate assembly to such bone structure further comprising driving bone fasteners through ones of the bone-fastener-receiving apertures and into such first and second bone structures, the bone support plate assembly further comprising cover apparatus spanning two such bone-fastener-receiving apertures, the cover apparatus automatically extending over a bone fastener which is driven, in a respective one of the bone-fastener-receiving apertures, and past retainer structure on the cover apparatus.

13. A method as in claim 8 wherein the bone support plate assembly is a spinal plate assembly and wherein the bone support plate assembly is attached to first and second vertebrae.

14. A method of installing a bone support plate assembly in a patient, the method comprising, in a surgical procedure:
   (a) providing a bone support plate assembly, comprising a plurality of plate members, including:
      (i) a first plate member, and
      (ii) a second plate member mounted to the first plate member,
      the plurality of plate members being mounted to each other and collectively defining at least one slidable interface, defined by a first lateral edge surface on a first one of the plate members and a second lateral edge surface on a second one of the plate members, each of the first and second lateral edge surfaces being in sliding communication with a respective other one of the plurality of plate members, the first plate member having a first distal end which defines a first end of the bone support plate assembly and a first proximal plate member end, the second plate member having a second distal end which defines a second end of the bone support plate assembly and a second proximal plate member end,
   (b) placing the bone support plate assembly at a mounting location in the patient;
   (c) attaching the first and second plate members to first and second different bone structures;
   (d) during the surgical procedure, releasing from fixation any internal plate assembly structure which internal plate assembly structure is disposed between the first and second ends of the bone support plate assembly, and which internal plate assembly structure is fixing the length of the bone support plate assembly by frictional engagement, or threaded coupling engagement, and which plate assembly structure is, by frictional engagement, or threaded coupling engagement, impeding sliding of respective ones of the plate members with respect to each other such that the respective plate members can slide freely with respect to each other, in extension and retraction, after completion of the surgical procedure; and
   (e) accommodating post-procedural settling of such first and second bone structures with respect to each other without movement of either of the first and second plate members with respect to such bone structure to which the respective plate member is attached.

15. A method as in claim 14 wherein the bone support plate assembly is a spinal plate assembly and wherein the bone support plate assembly is attached to first and second vertebrae.

16. A method as in claim 14 further comprising bone-fastener-receiving apertures in the bone support plate assembly, the attaching of the so-assembled bone support plate assembly to such first and second bone structures further comprising driving bone fasteners through ones of the bone-fastener-receiving apertures and into such first and second bone structures, and wherein such first and second bone structures to which the attachment is made are first and second vertebrae.

17. A method as in claim 16 wherein such fixation comprises threaded coupling engagement structure, the method comprising releasing such threaded coupling engagement structure from threaded coupling engagement which impedes sliding of respective ones of the plate members with respect to each other.

18. A method as in claim 14, further comprising releasing frictional engagement structure from any frictional engagement which impedes sliding of respective ones of the plate members with respect to each other.

19. A method as in claim 14, further comprising bone-fastener-receiving apertures in the bone support plate assembly, the attaching of the so-assembled bone support plate assembly to such bone structure further comprising driving bone fasteners through ones of the bone-fastener-receiving apertures and into such first and second bone structures, the bone support plate assembly further comprising cover apparatus spanning two such bone-fastener-receiving apertures, the cover apparatus automatically extending over a bone fastener which is driven, in a respective one of the bone-fastener-receiving apertures, and past retainer structure on the cover apparatus.

20. A method of installing a bone support plate assembly in a patient, the method comprising, in a surgical procedure:
   (a) providing a bone support plate assembly which is not routinely assimilated by the patient's body, the bone support plate assembly comprising a plurality of plate members, including:
      (i) a first plate member, and
      (ii) a second plate member mounted to the first plate member,
      the plurality of plate members being mounted to each other and collectively defining at least one slidable interface, defined by a first lateral edge surface on a first one of the plate members and a second lateral edge surface on a second one of the plate members, each of the first and second lateral edge surfaces being in sliding communication with a respective other one of the plurality of plate members, the first plate member having a first distal end with defines a first end of the bone support plate assembly and a first plate member proximal end, the second plate member having a second distal end which defines a second end of the bone support plate assembly and a second plate member proximal end;
   (b) placing the bone support plate assembly at a mounting location in the patient;
   (c) attaching the bone support plate assembly to first and second different bones;
   (d) during the surgical procedure, releasing from fixation any internal bone support plate assembly fixation structure which is between the first and second ends of the bone support plate assembly, which fixation structure impedes, by friction between respective ones of the plate members, or by thread coupling, respective ones of the plate members from sliding freely with respect to each other in extension and retraction after completion of the surgical procedure; and (e) accommodating post-procedural settling of such first and second bones with respect to each other without movement of either of the first and second plate members with respect to such bone to which the respective plate member is attached.

21. A method as in claim 20 wherein the bone support plate assembly is a spinal plate assembly and wherein the bone support plate assembly is fastened to first and second underlying vertebrae.

22. A method as in claim 20 further comprising bone-fastener-receiving apertures in the bone support plate assembly, the attaching of the so-assembled bone support plate assembly to such first and second bones further comprising driving bone fasteners through ones of the bone-fastener-receiving apertures and into such first and second bones.

23. A method as in claim 22 wherein the first and second bones, to which the attachment is made, are first and second vertebrae.

24. A method as in claim 20 wherein the method provides long-term support of the bones and wherein each of the first and second plate members is made from material selected from the group consisting of titanium and stainless steel.

25. A method as in claim 20 comprising releasing any length fixation, effected by frictional engagement structure, from frictional engagement which impedes sliding of respective ones of the plate members with respect to each other.

26. A method as in claim 20, further comprising bone-fastener-receiving apertures in the bone support plate assembly, the attaching of the so-assembled bone support plate assembly to such bone structure further comprising driving bone fasteners through ones of the bone-fastener-receiving apertures and into such first and second bone structures, the bone support plate assembly further comprising cover apparatus spanning two such bone-fastener-receiving apertures, the cover apparatus automatically extending over a bone fastener which is driven, in a respective one of the bone-fastener-receiving apertures, and past retainer structure on the cover apparatus.

27. A method of installing a bone support plate assembly to bone structure in a patient, in a surgical procedure, the method comprising:

(a) placing the bone support plate assembly at a mounting location in the patient, the bone support plate assembly having a length and comprising a plurality of plate members, including a first plate member adapted to be mounted to a first bone and a second plate member adapted to be mounted to a second bone, the first plate member having a first distal end which defines a first end of the bone support plate assembly and a first proximal plate member end, the second plate member having a second distal end which defines a second end of the bone support plate assembly and a second proximal plate member end, the bone support plate assembly having an adjustable length between the first distal end and the second distal end, the plurality of plate members being slidingly engaged with each other such that respective adjacent ones of the plate members can slide with respect to each other, the bone support plate assembly comprising length fixation structure temporarily fixing the length of the bone support plate assembly:

(b) attaching the so-assembled bone support plate assembly to such first and second bones by attaching the first plate member to such first bone and attaching the second plate member to such second different bone;

(c) during the surgical procedure, evaluating the bone structure of the patient, and releasing, adjusting, and temporarily re-fixing the length of the bone support plate assembly in response to such evaluation, prior to completion of the attaching of the first and second plates to the first and second bones of the patient; and (d) after re-fixing the length of the bone support plate assembly, and during the surgical procedure, releasing from fixation any internal plate assembly structure which structure is fixing the length of the bone support plate assembly and thereby impeding sliding of respective ones of the plate members with respect to each other whereby, after such releasing, such plurality of plate members can slide freely with respect to each other, including after completion of the surgical procedure.

28. A method as in claim 27 wherein the releasing of the fixation after the re-fixing enables the plate members to slide freely with respect to each other, including after completion of the surgical procedure.

29. A method as in claim 27, the bone support plate assembly being made of material which is not routinely assimilated by the patient's body.

30. A method as in claim 27 wherein the releasing of the fixation after the re-fixing comprises releasing any length fixation, effected by threaded coupling structure, from coupling engagement which impedes sliding of respective ones of the plate members with respect to each other.

31. A method as in claim 27 wherein the releasing of the fixation after the re-fixing comprises releasing any length fixation, effected by frictional engagement structure, from frictional engagement which impedes sliding of respective ones of the plate members with respect to each other.

32. A method as in claim 27, further comprising bone-fastener-receiving apertures in said bone support plate assembly, the attaching of the so-assembled bone support plate assembly to such bone structure further comprising driving bone fasteners through ones of the bone-fastener-receiving apertures and into such first and second bone structures, said bone support plate assembly further comprising cover apparatus spanning two such bone-fastener-receiving apertures, said cover apparatus automatically extending over a bone fastener which is driven, in a respective one of the bone-fastener-receiving apertures, and past retainer structure on said cover apparatus.

33. A method as in claim 27 wherein the bone support plate assembly is a spinal plate assembly and wherein the bone support plate assembly is attached to first and second vertebrae.

* * * * *